United States Patent [19]

Lu et al.

[11] Patent Number: 5,728,640
[45] Date of Patent: Mar. 17, 1998

[54] PREPARATION OF SUPPORTED METALLOCENE/ALUMINOXANE SOLID CATALYST

[75] Inventors: Bing Lu; Jinmei Wang; Xiaoyu Hong; Zhenhua Jing, all of Beijing, China

[73] Assignee: China Petrochemical Corp. and Research Institute of Petroleum Processing Sinopec, Beijing, China

[21] Appl. No.: 677,952

[22] Filed: Jul. 10, 1996

[30] Foreign Application Priority Data

Jul. 14, 1995 [CN] China .................... CN95107481.4

[51] Int. Cl.⁶ .................... A01J 31/00; A01J 37/00; C08F 4/02; C08F 4/60
[52] U.S. Cl. .................... 502/107; 502/103; 502/109; 502/111; 502/117; 502/118; 502/125; 502/126; 556/175; 556/179; 556/160; 556/943
[58] Field of Search .................... 556/175, 179; 502/107, 109, 111, 118, 129, 125

[56] References Cited

U.S. PATENT DOCUMENTS

| | | | |
|---|---|---|---|
| 3,792,070 | 2/1974 | Jones et al. | 556/179 |
| 4,203,867 | 5/1980 | Bye | 502/107 |
| 4,474,704 | 10/1984 | Sawicki | 556/179 |
| 4,925,821 | 5/1990 | Chang | 502/107 |
| 5,006,500 | 4/1991 | Chang | 502/107 |
| 5,008,228 | 4/1991 | Chang | 502/111 |
| 5,276,117 | 1/1994 | Tomotsu et al. | 502/125 |
| 5,278,263 | 1/1994 | Burroway | 502/111 |
| 5,280,000 | 1/1994 | Kakugo et al. | 502/125 |
| 5,405,816 | 4/1995 | Burroway | 502/111 |
| 5,663,394 | 9/1997 | Roberg et al. | 556/179 |

FOREIGN PATENT DOCUMENTS

| | | |
|---|---|---|
| 0 206 794 A1 | 12/1986 | European Pat. Off. . |
| 0 226 463 A1 | 6/1987 | European Pat. Off. . |
| 0 269 987 A2 | 6/1988 | European Pat. Off. . |
| 0 279 586 A2 | 8/1988 | European Pat. Off. . |
| 0 285 443 A1 | 10/1988 | European Pat. Off. . |
| 0 293 815 A1 | 12/1988 | European Pat. Off. . |
| 0 294 942 A1 | 12/1988 | European Pat. Off. . |
| 783605 | 9/1957 | United Kingdom .......... 556/179 |
| WO87/03889 | 7/1987 | WIPO . |
| WO88/05057 | 7/1988 | WIPO . |
| WO88/05058 | 7/1988 | WIPO . |

OTHER PUBLICATIONS

R.C. Mehrotra et al., J. Indian Chem. Soc., vol. 39, No. 9, pp. 635–640, Sep. 1962.

*Primary Examiner*—Glenn Caldarola
*Assistant Examiner*—J. Pasterczyk

[57] ABSTRACT

A process for preparing a supported metallocene/aluminoxane solid catalyst comprises preparing a water-in-oil emulsion of water and an inert solvent by using an emulsifier, adding dropwise the emulsion to a solution of an organoaluminium compound in an inert solvent to carry out the reaction to obtain a suspension of the particulate aluminoxane, followed by adding a solution of a metallocene to the above suspension to support the metallocene on the aluminoxane. The solid catalyst thus obtained can be used in the polymerization and copolymerization of olefins. Polymerization can be carried out by slurry polymerization, bulk polymerization, gas phase polymerization, etc.

16 Claims, No Drawings

PREPARATION OF SUPPORTED METALLOCENE/ALUMINOXANE SOLID CATALYST

BACKGROUND OF THE INVENTION

The present invention relates to a process for preparing a supported metallocene/aluminoxane solid catalyst, more particularly, to a process for preparing a supported metallocene/aluminoxane solid catalyst with particulate aluminoxane is carrier.

Metallocene/aluminoxane as a well-known catalyst for the polymerization of olefins which has been generally considered important due to its good activity. However, the properties of the polymers are greatly affected by the polymerization process and the morphology of the catalyst in the polymerization system. It is disclosed in DE127133, EP226463, EP269987 and EP293815 that a polymer having a narrow molecular weight distribution and a specific steric structure can be obtained at a high yield by using a metallocene/aluminoxane catalyst, but the polymer obtained has a small particule size of about 1–50 μ because the catalyst is soluble in the polymerization solvent generally used in the above patents. Moreover, when a polymer of high molecular weight is prepared, the viscosity of the polymerization solution increases remarkably, and the yield of polymer decreases, the polymer obtained generally has a low density and a granular polymer and thus can hardly be obtained.

EP206794, EP285443, EP294942, WO8703889, WO8805057, and WO8805058 describe the preparation of granular polymers via gas phase polymerization or liquid bulk polymerization by using a metallocene and an aluminoxane supported on a porous inorganic material such as silica and alumina or an organic polymer such as polyethylene, polypropylene and polystyrene as carrier. However, the catalytic activity is low because of the limited amount of the catalyst supported on the inorganic material or the insufficient support of the catalyst on the polymer particulates. Besides, there is a heavy loss of catalyst components, particularly aluminoxane due to the insufficient support. Moreover, the inorganic material remains in the polymers and has an adverse effect on the properties of the polymers.

U.S. Pat. Nos. 5,006,500, 4,925,821 and 5,008,228 teach that a solid catalyst can be obtained by preparing an aluminoxane supported on silica gel through the reaction of aqueous silica gel and an alkyl aluminum, and supporting a metallocene on the silica gel. Such a catalyst can be used in gas phase polymerization but the property of the polymer obtained is affected by the introduction of the foreign carrier.

EP279586 discloses two processes for preparing particulate aluminoxane. One is by contacting a solution of an aluminoxane with a solvent in which the aluminoxane is insoluble or less soluble, precipitating the aluminoxane as suspended particulate, followed by vacuum concentration and filtering; the other is by spray drying of a solution of an aluminoxane. The particulate aluminoxane obtained is suspended in a solvent in which the aluminoxane is insoluble or less soluble, to which suspension a solution of a metallocene is added, and a supported metallocene/aluminoxane solid catalyst is obtained after filtering. A polymer having a high bulk density, uniform particle size distribution and narrow molecular weight distribution and containing less fine particulates can be obtained by using said catalyst in the polymerization of an olefin. However, a solution of an aluminoxane needs to be prepared previously for the preparation of particulate aluminoxane and the process for preparing the solid catalyst is very complicated.

The object of the invention is to provide a easily operated process for preparing a supported metallocene/aluminoxane solid catalyst with the particulate aluminoxane as carrier.

SUMMARY OF THE INVENTION

The present invention provides a process for preparing a supported metallocene/aluminoxane solid catalyst comprising preparing a water-in-oil emulsion of water and an inert solvent by using an emulsifier, adding dropwise the emulsion to a solution of an organoaluminium compound in an inert solvent to carry out the reaction to obtain a suspension of the particulate aluminoxane, and followed by adding a solution of a metallocene to the above suspension to support the metallocene on the aluminoxane.

DETAILED DESCRIPTION OF THE INVENTION

The particulate aluminoxane prepared by the process of the invention has linear or cyclic structure as shown by the chemical formula below:

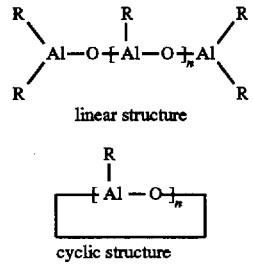

linear structure cyclic structure wherein

R represents $C_1$–$C_6$ alkyl such as methyl, ethyl, propyl, isopropyl, n-propyl, sec-butyl, isobutyl, tert-butyl, pentyl, hexyl, preferably $C_1$–$C_4$ alkyl, particularly methyl; and n represents an integer of 2–10, preferably 10–30.

According to the process of the invention, a supported metallocene aluminoxane solid catalyst can be prepared by (a) preparing a "water-in-oil" emulsion of water and an inert solvent by using an emulsifier in a known method, wherein the volume ratio of inert solvent:water:emulsifier is 100:0.5–10:0.1–1, preferably 100:1–5:0.2–0.5;

(b) dissolving an organoaluminium compound in an inert solvent to make a solution containing 5–30%, preferably 10–20% by weight of the organoaluminium compound;

(c) adding dropwise the above emulsion to the solution of the organoaluminium compound in a molar ratio of the organoaluminium compound to water in emulsion of 0.8–2:1, preferably 1–1.5:1, while stirring in an inert atmosphere at a temperature of −10°–40° C., preferably 0°–20° C., and at a rate of 0.2–20, preferably 0.5–5 ml/min, followed by heating the system to a temperature of 40°–80° C., preferably 40°–60° C., allowing the reaction to conduct for 1–4 hours to obtain a suspension of the particulate aluminoxane; and (d) adding a solution of a metallocene to the above suspension of the particulate aluminoxane in a molar ratio of the transition metal atom to aluminium atom of 1:100–10000, preferably 1:300–8000, particularly 1:500–5000, stirring the mixture at 0°–60° C. for 1–4 hours, and removing the solvent to produce the finished solid catalyst product.

The emulsifier used in the process of the invention is selected from the surfactants capable of forming water-in-oil emulsions, preferably those having hydrophilic-lypophilic balance (HLB) value of 2–6, preferably 3.5. Examples of suitable emusifiers include nonionic surfactants such as polyols and polyoxyethylenes. Such surfactants can react with organoaluminium compounds to form alkoxy aluminium compounds and do not adversely affect the use of the finished catalyst products in the polymerization of olefins.

Water used as starting material can be common water but distilled water or deionized water is preferably used.

By known emulsifying method we mean various methods generally used to form uniform fine emulsions, including simple stirring, high-speed stirring, colloidal mill grinding, homogenizer homogenizing and ultrasonic method, etc.

The inert solvents used to disperse the water and dissolve the organoaluminium may be the same or different and selected from the solvents in which the aluminoxane is insoluble or less soluble, for example, saturated hydrocarbons such as pentane, hexane, heptane, octane, decane, preferably hexane.

The organoaluminium compound used as starting material is selected from alkyl aluminium, alkoxy aluminium, aryl aluminium and alkyl aluminium halide, preferably trialkyl aluminium, more preferably tri($C_1$–$C_6$ alkyl) aluminium, particularly trimethyl aluminium.

The inert atmosphere used in the reaction may be nitrogen, helium or methane gas.

The metallocene compound suitable for the present invention is selected from the metallocenyl or substituted metallocenyl compounds of the IVB group transition metals in the Periodic Table, such as bicyclopentadienyl zirconium dichloride (bimetallocenyl zirconium dichloride), ethylidene biindenyl zirconium dichloride.

The solid catalysts prepared according to the process of the invention are suitable for use in the polymerization or copolymerization of olefins, which include ethylene, $C_3$–$C_{20}$ α-olefins, cyclic olefins and dienes. Suitable polymerization processes include slurry polymerization, liquid bulk polymerization, gas phase polymerization, etc. The solvent used in slurry polymerization may be a saturated aliphatic hydrocarbon or aromatic hydrocarbon, such as hexane, heptane, cyclohexane and toluene. The polymerization can be carried out under normal or high pressure and the polymerization pressure is typically from normal pressure to 10 MPa, preferably 0.2–5 MPa. The polymerization temperature can be $-78°$–$200°$ C., preferably $-20°$–$150°$ C. The amount of the solid catalyst used in the polymerization is generally $10^{-3}$–$10^{-2}$ mol, preferably $10^{-7}$–$10^{-3}$ mol, in the amount of the metal atom in the metallocene. The polymerization process may be continuous or batchwise. The molecular weight of the polymer can be controlled by known methods during polymerization, such as by the selection of the temperature and pressure, and introduction of hydrogen into the polymerization system.

The solid catalysts prepared according to the process of the invention can be used alone in the polymerization of olefins or in combination with organoaluminium compounds to further increase the activity or eliminate the poisoning of the catalysts. The organoaluminium compounds preferably used herein are triethyl aluminium and triisobutyl aluminium.

The process of the present invention can provide supported metallocene/aluminoxane solid catalysts, at a high yield and with good reproducibility, directly from organoaluminium compounds as starting materials and require simple apparatus which are easy to operate. The solid catalysts obtained have high activity and are suitable for a variety of polymerization processes. The polymers obtained from the polymerization of olefins catalyzed by the catalysts of the invention have good granular morphology and contain less fine particules.

The following examples are given to further illustrate the invention and not intended to limit the scope of the invention.

EXAMPLE 1

Preparation of the Solid Catalyst 100 ml of n-hexane, 0.2 ml of sorbitan monooleate (tradename Span-80, HLB 4.3, Shanghai chemical reagents factory) and 2 ml of water were added successively under nitrogen to a 200 ml flask equipped with a magnetic bar. The mixture was stirred at 20 rpm on a magnetic stirrer to form an emulsion. A 500 ml three-neck flask equipped with a stirrer and a gas outlet was charged under nitrogen with 100 ml of 15 wt. % solution of trimethyl aluminium in hexane (manufactured by Tokyo Kasei Co. Ltd.) and 50 ml of n-hexane. To the solution was added dropwise the above emulsion at 1 ml/min while thoroughly stirring at room temperature until the molar ratio of aluminium to water was 1.3. Then the system was heated to 40° C. and the reaction was continuously stirred for 4 hours to give a suspension containing white flocculent methyl aluminoxane (MAO).

It is shown by the observation of small amount of the suspension under optical microscope that the aluminoxane appears as quasispherical particulates having particle size of 5–20 μ.

To a 100 ml reaction flask equipped with a stirrer was added, under nitrogen, 50 ml of the suspension of the particulate aluminoxane prepared as described above, followed by 5 ml of $2.3 \times 10^{-3}$M solution of bis-cyclopentadienyl zirconium dichloride ($Cp_2ZnCl_2$, Aldrich) in toluene. After the mixture was stirred for 4 hours at room temperature, the solvent was removed in vacuum to yield a 1.4 g solid catalyst in white powder.

Polymerization of Ethylene Under Normal Pressure

A 500 ml of three-neck flask equipped with a stirrer was purged with high-purity nitrogen and changed into ethylene atmosphere, to which was added 100 ml of toluene and 82.5 mg of the solid catalyst prepared as described above. Ethylene was continuously fed in and allowed to polymerize at 40° C. for 1 hour under a normal pressure in the flask. The product was treated with ethanol, filtered and vacuum dried to yield 0.5 g polyethylene. The polymerization activity of the catalyst was $7.4 \times 10^{-5}$ g polyethylene/mole zirconium·hour (g PE/mol Zr·hr). The polymer has good granular morphology and contains no fine particles.

Polymerization of Ethylene Under High Pressure

To a 1 liter stainless steel autoclave purged with high-purity nitrogen was added 300 ml of n-hexane and 513.4 mg of the catalyst prepared as described above. Ethylene was allowed to polymerize at 40° C. for 1 hour while keeping its pressure at 1.0 MPa, to give 5.6 g polyethylene. The polymerization activity was $1.3 \times 10^6$ g PE/mol Zr·hr. The polymer has good granular morphology.

EXAMPLE 2

The procedure of example 1 was repeated except that 5 ml of $1.2 \times 10^{-3}$M solution of ethylidene bisindenyl zirconium dichloride (Et(Ind)$_2$Zr$_2$, prepared as described in J. Organomet. Chem., 288, 63–67(1985)) in toluene was used instead of 5 ml of 2.3×10$^{-3}$M solution of Cp$_2$ZrCl$_2$ in toluene, to give yield 1.3 g solid catalyst in brown-yellowish powder.

Following the procedure of example 1, the polymerizations of ethylene under normal and high pressure were carried out using the solid catalyst prepared as described above. The parameters and results of the polymerizations are shown in Table 1. The melting point of the polymer was determined by differential scanning calorimetry (DSC).

EXAMPLE 3

The procedure of example 1 was repeated except that 20 ml of 1.2×10$^{-3}$M solution of Et(Ind)$_2$ZrCl$_2$ toluene was used instead of 5 ml of 2.3×10$^{-3}$M solution of Cp$_2$ZrCl$_2$ in toluene, to yield 1.4 g solid catalyst in brown-yellowish powder.

Following the procedure of example 1, the polymerization of ethylene under normal and high pressure were carried out using the solid catalyst prepared as described above. The parameters and results of the polymerizations are shown in Table 1.

| Example No. | 2 | | 3 | |
|---|---|---|---|---|
| Polymerization Pressure | NP* | 1MPa | NP | 1MPa |
| Amount of the solid catalyst, mg | 76.4 | 431.8 | 84.1 | 326.7 |
| Amount of the polymer, g | 0.7 | 6.8 | 3.2 | 18.5 |
| Polymerization activity, g PE/mol Zr · hr | 2.0 × 10$^6$ | 3.4 × 10$^6$ | 2.2 × 10$^6$ | 3.3 × 10$^6$ |
| Morphology of the polymer | fluffy granules | good granules | fluffy granules | good granules |
| Melting point of the polymer, °C. | 134.9 | 135.2 | 133.5 | 134.7 |
| Bulk density of the polymer, g/cm$^3$ | — | 0.42 | — | 0.43 |

*NP = normal pressure

EXAMPLE 4

Copolymerization of Ethylene and Hexane Under Normal Pressure

The polymerization under normal pressure was carried out according to the similar procedure as described in example 1 except that 109.3 mg of the solid catalyst prepared in example 2 was used instead of 82.5 mg of the solid catalyst in example 1 and 10 ml of hexene was added, to give 0.5 g copolymer as fluffy granules. The polymerization activity was 9.0×10$^5$ g PE/mol Zr·hr. The copolymer has a melting point of 125.1° C. as determined by DSC and a density of 0.913 g/cm$^3$ as determined by density gradient tube.

EXAMPLE 5

Preparation of the Solid Catalyst

The procedure of example 1 was repeated except that 10 ml of 2.3×10$^{-3}$M solution of dimethylsilylene disindenyl zirconium dichloride (Me$_2$Si(Ind)$_2$ZrCl$_2$, prepared as described in U.S. Pat. No. 5,103,030) in toluene was used instead of 5 ml of 2.3×10$^{-3}$M solution of Cp$_2$ZrCl$_2$ in toluene, to yield 1.4 g solid catalyst in brown-yellowish powder.

Liquid Bulk Polymerization of Propylene Under High Pressure

A 1 liter stainless steel autoclave was purged thoroughly with high-purity nitrogen and then changed into propylene atmosphere, to which was added 563.7 mg of the solid catalyst prepared as described above, followed by 600 ml of liquid propylene. The polymerization was carried out at 40° C. while being stirred in a closed system for 2 hours. When the polymerization was completed, the mixture was discharged and the product was recovered and dried to yield 11.1 g polypropylene.

The polymerization activity was 1.2×10$^6$ g PP/mol Zr·hr. The polypropylene appeared as good granules, and had an apparent bulk density of 0.44 g/cm$^3$ and a melting point of 140° C. It was demonstrated by $^{13}$C-NMR that the polypropylene contains 90% of diad mm.

We claim:

1. A process for preparing a supported metallocene/aluminoxane solid catalyst which comprises the steps of:
   a) preparing a water-in-oil emulsion by combining a first inert solvent, water, and emulsifier,
      wherein the volume ratio of said first inert solvent, water, and emulsifier is about 100:0.5 to 10:0.1 to 1;
   b) dissolving an organoaluminum compound in a second inert solvent to make a solution having about 5 to about 30% by weight of the organoaluminum compound;
   c) adding dropwise said emulsion to said solution of the organoaluminum compound in a molar ratio of the organoaluminum compound to water in emulsion of about 0.8 to 2:1 in an inert atmosphere at a temperature of about −10° to about 40° C. and a rate of about 0.2 to about 20 ml/min, followed by heating the resulting solution to a temperature of about 40° to about 80° C. and allowing the reaction to proceed for about 1 to about 4 hours to obtain a suspension of a particulate aluminoxane; and
   d) adding a solution of a transition metal metallocene to said suspension of the particulate aluminoxane in a molar ratio of transition metal atom to aluminum atom of about 1:100 to 10,000 at about 0° to about 60° C. for about 1 to about 4 hours and removing the solvent to form said catalyst,
      wherein said transition metal is selected from a metal in Group IV B of the Periodic Table.

2. The process according to claim 1, wherein said volume ratio of inert solvent, water, and emulsifier is about 100:1 to 5:0.2 to 0.5.

3. The process according to claim 1, wherein said solution made in step b) has about 10 to about 20% by weight of the organoaluminum compound.

4. The process according to claim 1, wherein said molar ratio of the organoaluminum compound to water in emulsion is about 1 to 1.5:1.

5. The process according to claim 1, wherein said addition of step c) is carried out at a temperature of about 0° to about 20° C. and a rate of about 0.5 to about 5 ml/min.

6. The process according to claim 1, wherein said reaction after said addition in step c) is carried out at a temperature of about 40° to about 60° C.

7. The process according to claim 1, wherein said molar ratio of the transition metal atom in the metallocene to aluminum atom is about 1:300 to 8,000.

8. The process according to claim 1, wherein said emulsifier is a polyol nonionic surfactant having a hydrophilic-lypophilic balance value of about 2 to about 6.

9. The process according to claim 1, wherein said first inert solvent and said second inert solvent comprise those solvents in which said aluminoxane is insoluble or slightly soluble.

10. The process according to claim 1, wherein said organoaluminum compound is selected from the group consisting of alkyl aluminum, alkoxy aluminum, aryl aluminum and alkyl aluminum halide.

11. The process according to claim 7, wherein said molar ration of the transition metal atom in the metallocene to aluminum atom is about 1:500 to 5,000.

12. The process according to claim 8, wherein said emulsifier is a polyol nonionic surfactant having a hydrophilic-lypophilic balance value of about 3 to about 5.

13. The process according to claim 9, wherein said first and second inert solvents are saturated hydrocarbon compounds.

14. The process according to claim 13, wherein said saturated hydrocarbon compounds are hexane.

15. The process according to claim 10, wherein said organoaluminum compound is a trialkyl aluminum.

16. The process according to claim 15, wherein said trialkykl aluminum is trimethyl aluminum.

* * * * *